(12) United States Patent
Kazama et al.

(10) Patent No.: US 9,389,169 B2
(45) Date of Patent: Jul. 12, 2016

(54) SURFACE INSPECTION METHOD AND SURFACE INSPECTION APPARATUS FOR STEEL SHEET COATED WITH RESIN

(75) Inventors: Akira Kazama, Tokyo (JP); Kaoru Tanaka, Tokyo (JP); Jun Sakai, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 325 days.

(21) Appl. No.: 13/637,921

(22) PCT Filed: Feb. 25, 2011

(86) PCT No.: PCT/JP2011/054266
§ 371 (c)(1),
(2), (4) Date: Nov. 12, 2012

(87) PCT Pub. No.: WO2011/122185
PCT Pub. Date: Oct. 6, 2011

(65) Prior Publication Data
US 2013/0050470 A1  Feb. 28, 2013

(30) Foreign Application Priority Data
Mar. 30, 2010  (JP) .................................. 2010-076939

(51) Int. Cl.
*H04N 7/18* (2006.01)
*G01N 21/21* (2006.01)
(Continued)

(52) U.S. Cl.
CPC ............. *G01N 21/21* (2013.01); *G01N 21/8422* (2013.01); *G01N 21/8901* (2013.01); *G01N 21/8914* (2013.01); *G01N 2021/8918* (2013.01)

(58) Field of Classification Search
CPC .................................................. G01N 2021/896
USPC ............................................................ 348/92
See application file for complete search history.

(56) References Cited

U.S. PATENT DOCUMENTS 7,646,546 B1 *  1/2010  O'Shaughnessy et al. ... 359/669

FOREIGN PATENT DOCUMENTS

JP         8-94542 A      4/1996
JP         09-159621 A    6/1997
(Continued)

OTHER PUBLICATIONS

International Search Report dated May 31, 2011 issued in International Appln. No. PCT/JP2011/054266.
(Continued)

*Primary Examiner* — Christopher S Kelley
*Assistant Examiner* — Jonathan Messmore
(74) *Attorney, Agent, or Firm* — Holtz, Holtz & Volek PC

(57) ABSTRACT

A surface inspection method for a steel sheet coated with a resin, includes irradiating the steel sheet with sheet-like light, which has been linearly polarized at a predetermined polarization angle, at an incidence angle different from Brewster's angle of the coating by a predetermined angle or greater; and imaging linearly-polarized light of a polarization angle of 0 degrees at an acceptance angle different from a regular reflection angle of incident light by a predetermined angle. Accordingly, it is not necessary to change the incidence angle and the acceptance angle depending on resin components and it is possible to inspect a substrate steel surface of the steel sheet highly accurately without observing abnormalities in the coating itself.

4 Claims, 5 Drawing Sheets

(51) Int. Cl.
*G01N 21/84* (2006.01)
*G01N 21/89* (2006.01)

(56) References Cited

FOREIGN PATENT DOCUMENTS

| JP | 10-282014 A | | 10/1998 |
|---|---|---|---|
| JP | 11-248642 A | | 9/1999 |
| JP | 11295239 A | | 10/1999 |
| JP | 11295241 A | * | 10/1999 |
| JP | 2000-221143 A | | 8/2000 |
| JP | 2002-181723 A | | 6/2002 |
| JP | 2002-214150 A | | 7/2002 |
| JP | 2005-189113 A | | 7/2005 |
| JP | 2005189113 A | * | 7/2005 |
| JP | 2007-057487 A | | 3/2007 |
| JP | 2008-26060 A | | 2/2008 |
| JP | 2008026060 A | * | 2/2008 |
| JP | 2008-267972 A | | 11/2008 |
| SU | 1476359 A1 | | 4/1989 |

OTHER PUBLICATIONS

Taiwanese Office Action dated Jan. 13, 2014 in counterpart Taiwanese Application No. 100106668.
Russian Office Action dated Dec. 16, 2013 in counterpart Russian Application No. 2012141228/28(066438).
Extended European Search Report dated Apr. 17, 2015, issued in counterpart European Application No. 11762425.4.
Japanese Office Action (and English translation thereof) dated Sep. 1, 2015, issued in counterpart Japanese Application No. 2011-045436.
Korean Office Action (and English translation thereof) dated Aug. 21, 2015, issued in counterpart Korean Application No. 10-2014-7034682.

* cited by examiner

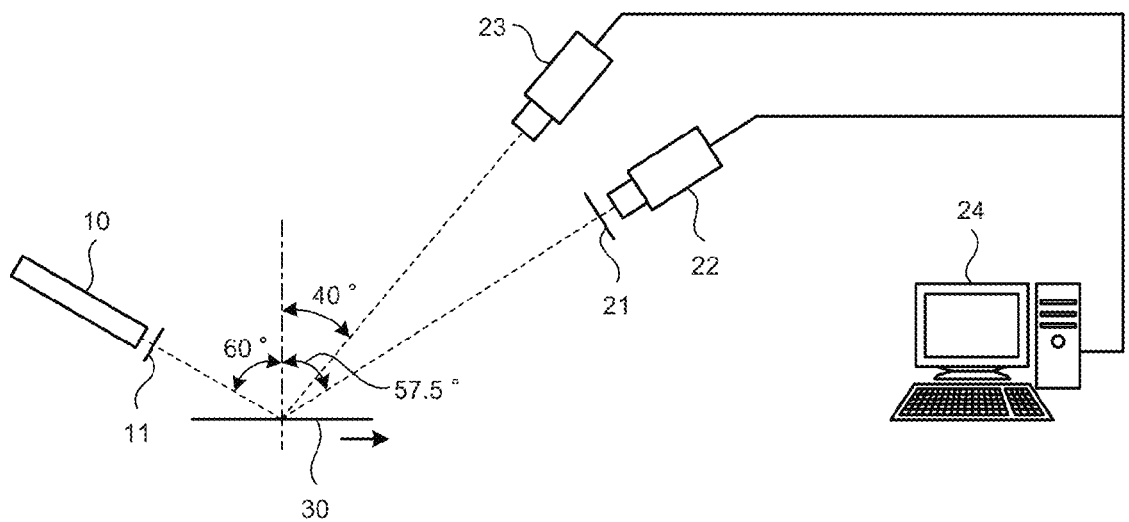
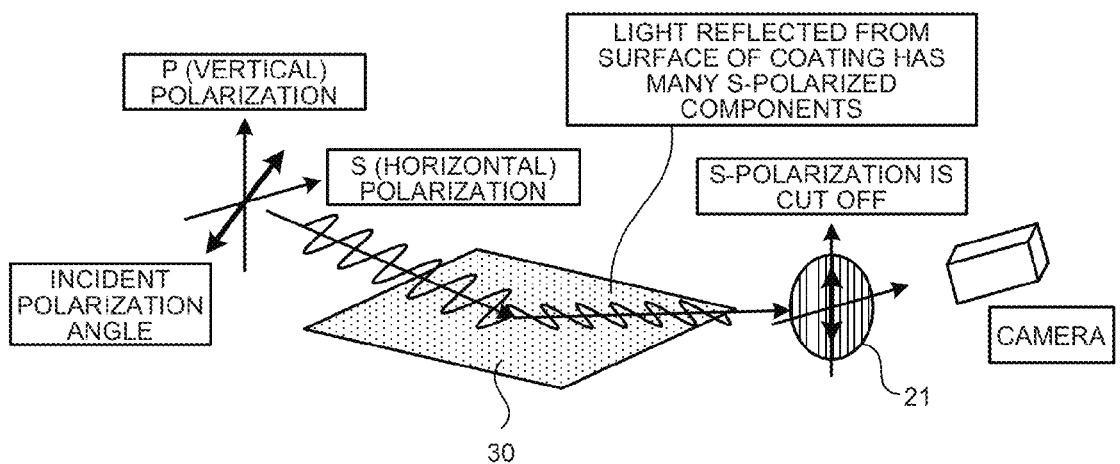

SURFACE INSPECTION METHOD AND SURFACE INSPECTION APPARATUS FOR STEEL SHEET COATED WITH RESIN

This application is a U.S. National Phase Application under 35 USC 371 of International Application PCT/JP2011/054266 filed Feb. 25, 2011.

FIELD

The present invention relates to a surface inspection method and a surface inspection apparatus for a steel sheet coated with a transparent resin.

BACKGROUND

In surface inspection of steel sheets, inspection is usually performed using both regular reflection and diffuse reflection. When a usual apparatus not using polarization is used in inspection of a resin-coated steel sheet, because reflection by a surface of the coating in regular reflection is too strong and substrate steel surface of the steel sheet is hidden, detection of a defect becomes difficult. This is a phenomenon that is the same as the phenomenon in which the bottom of a river becomes invisible because reflection by the water surface is strong when a surface of the river is observed in the daytime, for example.

There is a technique, using a polarizing filter, to suppress reflection of S-polarized light, which is polarized parallel to a surface of a steel sheet. This technique can be implemented by using, on a light-receiving side, a polarizing filter that transmits only P-polarized light polarized in a direction perpendicular to the surface of the steel sheet. This is a phenomenon that is the same as the phenomenon in which the bottom of water becomes visible by suppressing reflection of S-polarized light from the water surface with widely commercially available polarizing glasses.

Inspection methods which industrially implement this are disclosed in Patent Literature 1 and Patent Literature 2. In these, angles of light sources are set to a special angle called Brewster's angle. Since reflection of P-polarized light becomes zero at the Brewster's angle, reflection from a surface of a coating is suppressible by providing, on a light-receiving side, a filter of a P-polarization direction that cuts off S-polarized light.

CITATION LIST

Patent Literature

Patent Literature 1: Japanese Patent Application Laid-open No. 2008-026060
Patent Literature 2: Japanese Patent Application Laid-open No. 2002-214150

SUMMARY

Technical Problem

The Brewster's angles set in the inspection methods disclosed in Patent Literature 1 and Patent Literature 2 have a characteristic of varying depending on the refractive index of the resin coating. Accordingly, when components of a coating are changed, the angle of the light source must be reset each time. Since on the light-receiving side, the acceptance angle corresponding to the angle of the light source usually needs to be set, a change in the acceptance angle on the light-receiving side is not avoidable. As a result, the configuration of the apparatus becomes complicated. On the other hand, according to findings by the inventors of the present invention, even if S-polarized light is able to be cut off, at a regular reflection angle, an abnormality of the resin coating itself in a thickness, in the components, or of some kind is strongly observed. Therefore, this type of surface inspection of a steel sheet coated with a resin has the next two technical problems to be solved.

(1) An incidence angle of a light source and an acceptance angle must be changed depending on resin components.

(2) In light reception of regular reflection, abnormality in a coating portion becomes conspicuous and observation of substrate steel surface of a steel sheet becomes difficult.

The present invention has been made to solve these problems and an object thereof is to provide a surface inspection method and a surface inspection apparatus for a steel sheet coated with a resin in which an incidence angle or the like is not required to be changed depending on resin components and enables accurate inspection of substrate steel surface of a steel sheet.

Solution to Problem

According to the present invention, a surface inspection method for a steel sheet coated with a resin is a surface inspection method of imaging the steel sheet coated with the resin and inspecting for a surface defect, the method including the steps of: irradiating, at a predetermined incidence angle, the steel sheet with sheet-like light that has been linearly polarized at a predetermined polarization angle; and imaging linearly-polarized light with a polarization angle of 0 degrees at an acceptance angle that has been shifted by a predetermined angle with respect to a regular reflection angle of incident light. The predetermined incidence angle is preferably different from Brewster's angle of the coating by a predetermined angle (for example, 1 degree) or greater. Preferably, the method further includes the step of imaging a surface of the steel sheet at an angle shifted by a predetermined angle (for example 10 degrees or greater) from the regular reflection angle.

According to the present invention, a surface inspection apparatus for a steel sheet coated with a resin is a surface inspection apparatus that images the steel sheet coated with the resin and inspects for a surface defect, the apparatus including: a light source that irradiates, at a predetermined incidence angle, the steel sheet with sheet-like light that has been linearly polarized at a predetermined polarization angle; and a first imaging device that images linearly-polarized light with a polarization angle of 0 degrees at an acceptance angle that has been shifted by a predetermined angle with respect to a regular reflection angle of incident light. The incidence angle of the light source is preferably set to an angle that is different from Brewster's angle of the resin coating by a predetermined angle (for example, 1 degree) or greater. Preferably, the apparatus further includes a second imaging device that images a surface of the steel sheet at an angle shifted by a predetermined angle (for example 10 degrees or greater) from the regular reflection angle.

Advantageous Effects of the Present Invention

According to the present invention, a steel sheet is irradiated, at a predetermined incidence angle, with sheet-like light that has been linearly polarized at a predetermined polarization angle, and linearly-polarized light at a polarization angle of about 0 degrees is imaged at an acceptance angle that is shifted by a predetermined angle from a regular reflection angle of incident light. Accordingly, according to the present invention, reflection from the coating is suppressed, abnormality in the coating itself is not observed, substrate steel surface of the steel sheet is observable, and highly accurate inspection becomes possible. According to the present invention, moreover, an incidence angle and an acceptance angle do not need to be changed depending on resin components and accurate inspection of substrate steel surface of a steel sheet becomes possible. According to preferable modes of the present invention, a steel sheet is irradiated with sheet-like light at an incidence angle different from Brewster's angle of a coating by a predetermined angle (for example, 1 degree) or greater, and thus inspection with stable reflection becomes possible.

BRIEF DESCRIPTION OF DRAWINGS

FIG. 1 is a block diagram illustrating a configuration of a surface inspection apparatus for a steel sheet coated with a resin according to an embodiment of the present invention.

FIG. 2 is a diagram illustrating a polarization state of an optical system where a polarizing filter is arranged on a light-receiving side.

DESCRIPTION OF EMBODIMENTS

Figure 3A:
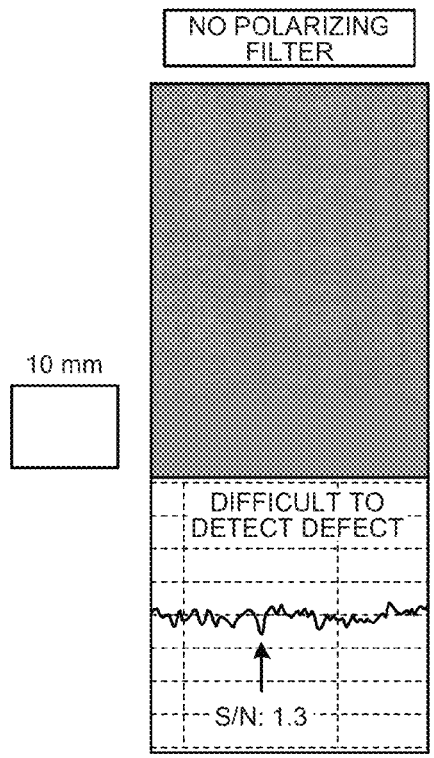
FIG. 3A is a diagram illustrating an example of a sample defect image when the optical system of FIG. 2 does not include the polarizing filter.

FIG. 1 is a block diagram illustrating a configuration of a surface inspection apparatus for a steel sheet coated with a resin (hereinafter, simply referred to as a steel sheet) according to an embodiment of the present invention. The surface inspection apparatus is applied to inspection for any defects on a surface of the steel sheet immediately before being wounded into a coil, after being subjected to rolling, annealing, resin coating, and the like. The resin coating is formed on both surfaces of the steel sheet for insulating from upper and lower adjacent steel sheets upon use in a transformer or the like. Both of the surfaces of the steel sheet may be inspected for any defects, but an example where one of the surfaces is inspected is illustrated in FIG. 1 for convenience.

The surface inspection apparatus includes, on a light-emitting side, a sheet-like light source 10 and a polarizing filter 11. The sheet-like light source 10 includes a plurality of lamps, an optical fiber bundle (hereinafter referred to as a bundle fiber) arranged line-like per lamp, and a cylindrical lens, and is formed to emit sheet-like (line-like) light as a whole. The sheet-like light source 10 is arranged so that an incidence angle on a steel sheet 30 is, for example, 60 degrees and irradiates the steel sheet 30 with sheet-like light via the polarizing filter 11. The reason for setting the incidence angle to 60 degrees is to cause the incidence angle to be different from Brewster's angle of the coating of the steel sheet 30 by a predetermined angle (for example, 1 degree) or greater. A component of the resin coating is, for example, a transparent acrylic resin and Brewster's angle thereof is 56.1 degrees. Accordingly, the incidence angle of the light source on the steel sheet 30 is set to 60.0 degrees. The polarizing filter 11 is formed of, for example, a 45-degree polarizing filter. The polarizing filter 11 is arranged between the sheet-like light source 10 and the steel sheet 30, close to an emission face of the sheet-like light source 10 for example, and linearly polarizes the sheet-like (line-like) light from the sheet-like light source 10. As for polarization angles, a direction of a normal line of the steel sheet is 0 (zero) degrees.

The surface inspection apparatus includes, on a light-receiving side, a polarizing filter 21, a semi-regular reflection camera 22, a diffusion camera 23, and an image processing device 24. The polarization angle of the polarizing filter 21 is set to, for example, about 0 degrees (from −5 degrees to 5 degrees). The semi-regular reflection camera 22 is formed of a line sensor. The semi-regular reflection camera 22 is arranged so that an acceptance angle thereof is, for example, 57.5 degrees and captures an image based on reflected light from the steel sheet 30 via the polarizing filter 21. The diffusion camera 23 is formed of a line sensor and is arranged so that an acceptance angle thereof is in a range of 30 degrees to 50 degrees. In this example, it is arranged so that the acceptance angle thereof is 40 degrees. In common, a polarizing filter is not arranged between the diffusion camera 23 and the steel sheet 30. The image processing device 24 receives and performs image processing on outputs from the semi-regular reflection camera 22 and the diffusion camera 23 and determines whether or not a surface defect is present. The semi-regular reflection camera 22 corresponds to a first imaging device of the present invention and the diffusion camera 23 corresponds to a second imaging device of the present invention.

The technical significance of the arrangement of the polarizing filter 21 and the semi-regular reflection camera 22 in FIG. 1 will be described below with reference to FIGS. 2 to 4 and the technical significance of the arrangement of the diffusion camera 23 in FIG. 1 will be described below with reference to FIGS. 5A AND 5B.

FIG. 2 is a diagram illustrating a polarization state of an optical system when the polarizing filter 21 is arranged on the light-receiving side. The reflected light from a surface of the coating of the steel sheet 30 includes many S-polarized components. Accordingly, by cutting off the S-polarized light by the polarizing filter 21, the reflected light from the surface of the coating becomes half or less, and thus the reflection from the surface of the coating is suppressed and substrate steel surface of the steel sheet 30 becomes conspicuous.

Figure 3B:
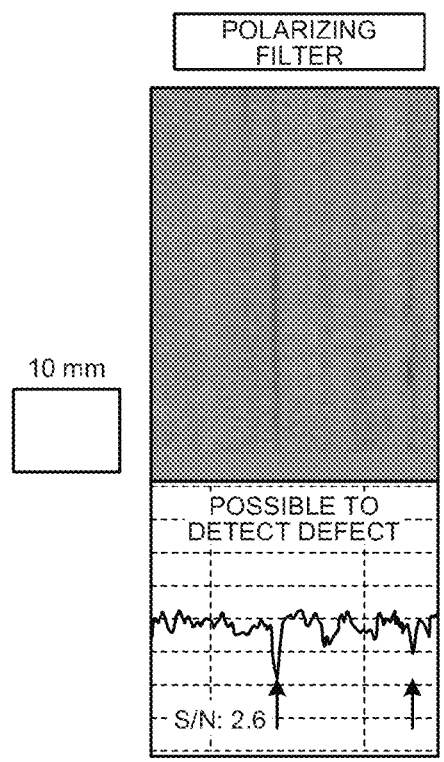
FIG. 3B is a diagram illustrating an example of a sample defect image when the optical system of FIG. 2 includes the polarizing filter.

FIGS. 3A and 3B are examples of a defect image of the same sample when the optical system of FIG. 2 does not include or does include the polarizing filter. As illustrated in FIG. 3A, when the polarizing filter 21 is not there, the ratio S/N between a defect signal and a noise signal is 1.3 and defects are difficult to be seen. However, as illustrated in FIG. 3B, when the polarizing filter 21 is there, the S/N is 2.6 and the defects are conspicuous.

Figure 4:
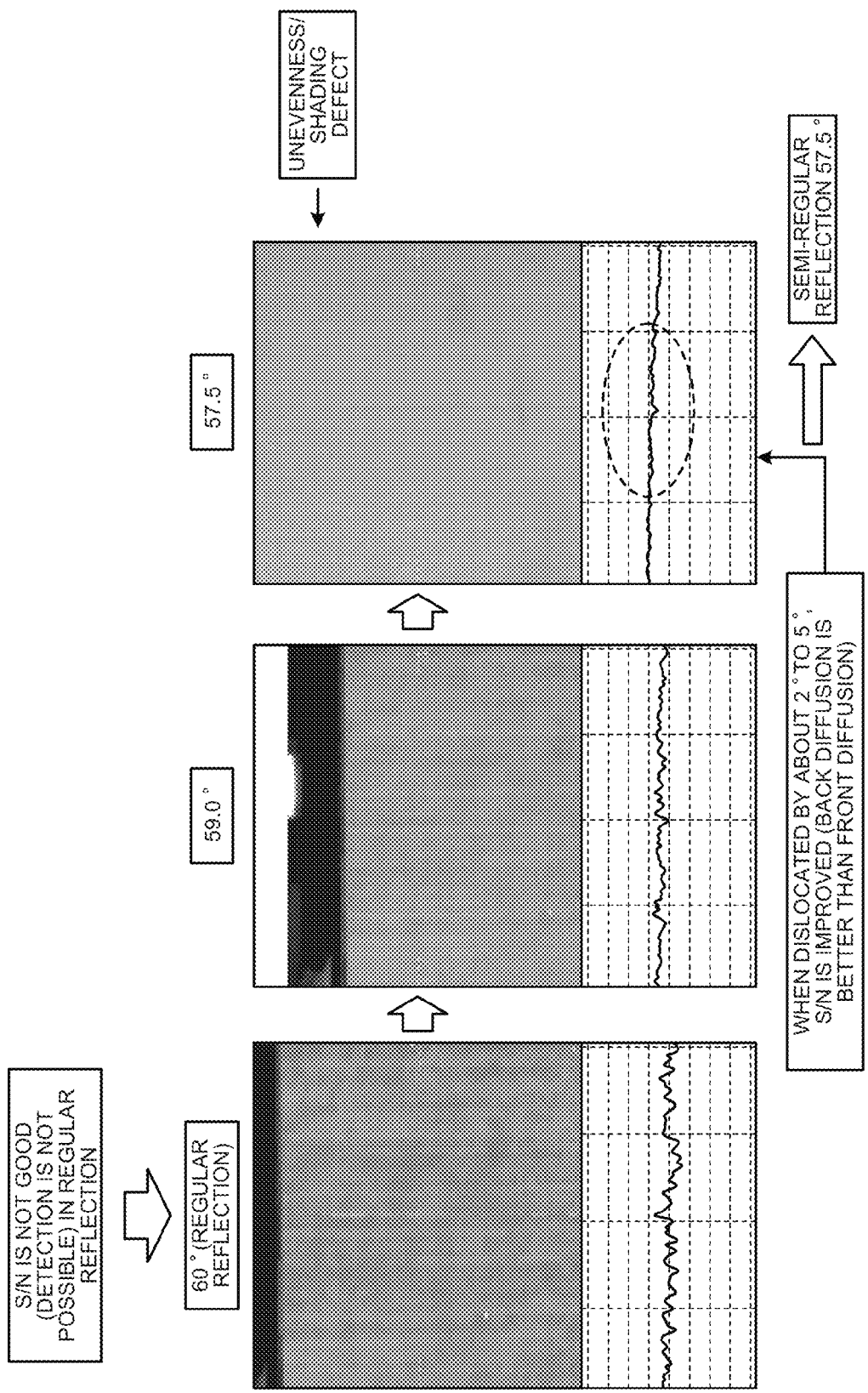
FIG. 4 is a diagram illustrating a relation between an acceptance angle of a semi-regular reflection camera and a defect image.

FIG. 4 is a diagram illustrating a relation between the acceptance angle of the semi-regular reflection camera 22 and a defect image. FIG. 4 illustrates examples of an image of a defect when the acceptance angle of the camera is set to 60 degrees (regular-reflection light reception), 59 degrees, and 57.5 degrees. When the acceptance angle of the camera is 60 degrees, the S/N is low and a defect is not detectable. On the contrary, as the acceptance angle of the camera is gradually shifted to be set to 59 degrees and 57.5 degrees, noise considered to be caused by heterogeneity of the resin coating becomes inconspicuous and the S/N increases. It has been confirmed that when the acceptance angle of the camera is shifted from a regular reflection position by, for example, about 2 degrees to 5 degrees, the S/N is improved. In this case, it has also been confirmed that back diffusion is better than front diffusion, that is, dislocating in a descending direction of the acceptance angle is better. In the present invention, as described, a state of being shifted by the above angle from the regular reflection position is called a semi-regular reflection. When slanted by 5 degrees or greater, imaging becomes that of the diffuse reflection rather than the regular reflection, and thus detection of a defect to be detected by the semi-regular reflection may become impossible.

Figure 5A:
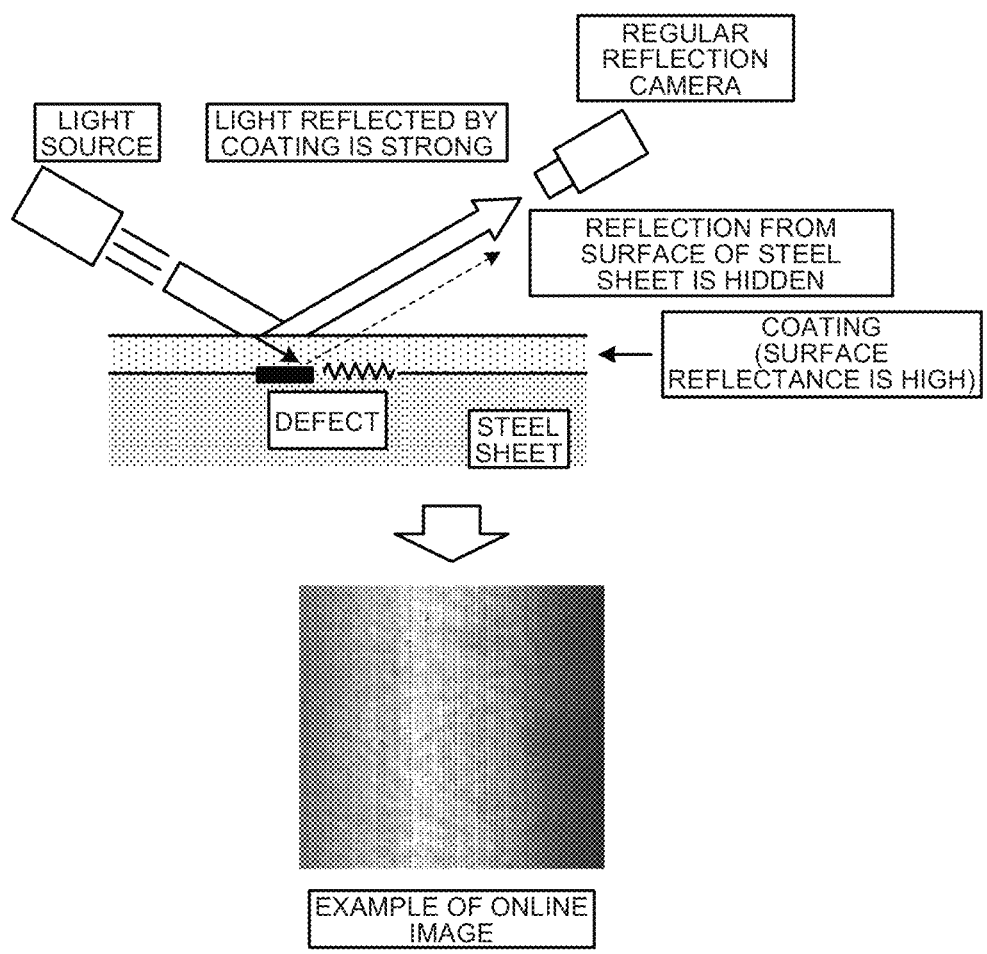
FIG. 5A is a diagram illustrating an example of an image of a steel sheet coated with a resin when a camera is arranged at a regular reflection position.
Figure 5B:
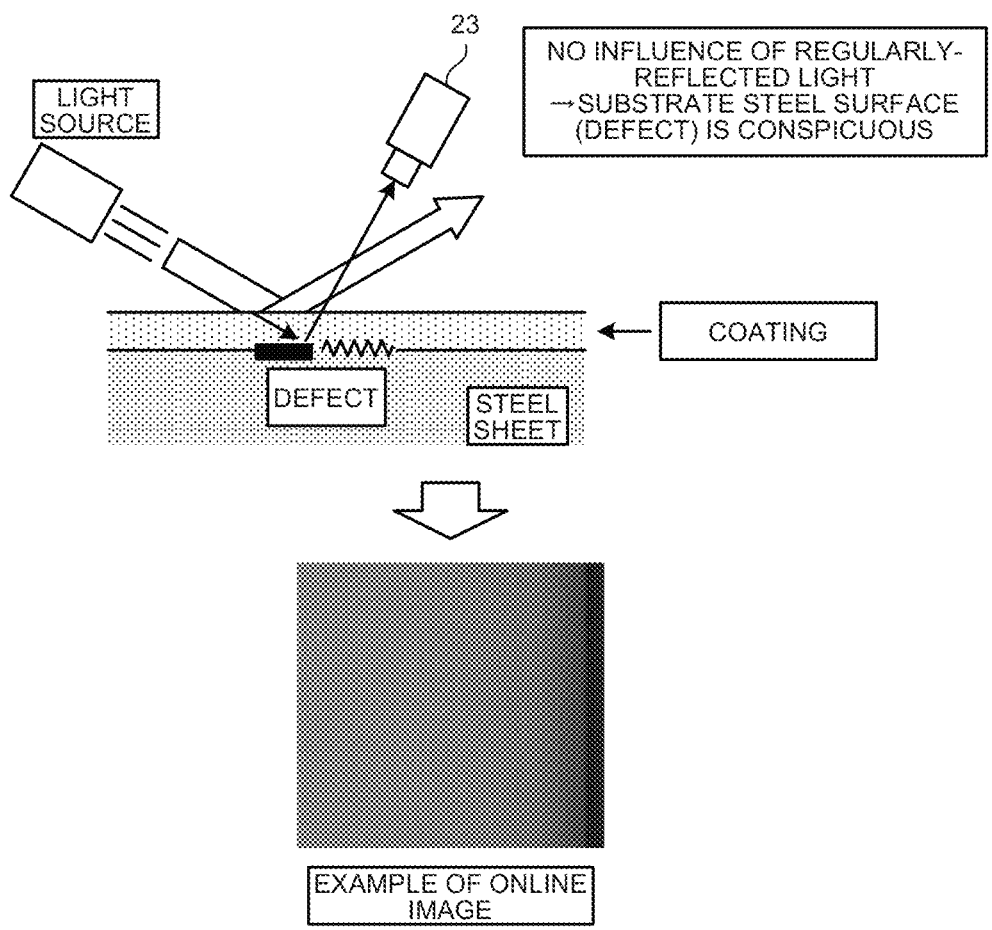
FIG. 5B is a diagram illustrating an example of an image of a steel sheet coated with a resin when a camera is arranged at a position at which diffused light is received.

FIGS. 5A and 5B are diagrams illustrating acceptance angles of the diffusion camera 23. As illustrated in FIG. 5A, when the camera is arranged at the regular reflection position, the light reflected by the coating is strong and the surface reflection of the steel sheet is hidden. As a result, in an image captured by the camera, coating unevenness is visible, but the substrate steel surface (defect) is invisible. However, as illustrated in FIG. 5B, when the camera is arranged at a position (at an angle shifted from the regular-reflection acceptance angle by a predetermined angle (for example, 10 degrees or greater)) where diffused light is received, influence by the regularly-reflected light disappears and the substrate steel surface (defect) becomes conspicuous. The images in FIGS. 5A and 5B are those of a non-defective portion imaged.

Now that from the above description, the technical significance of the polarizing filter 21, the semi-regular reflection camera 22, and the diffusion camera 23 in this embodiment has been disclosed, the image processing device 24 will be described below with reference to FIG. 1 again.

The image processing device 24 performs image processing on image signals captured by the semi-regular reflection camera 22 and the diffusion camera 23 and determines whether or not a surface defect is present by comparing a brightness value with a predetermined threshold value. The steel sheet is welded upstream of an inspection position, therefore continuous at the inspection position, then cut downstream of the inspection apparatus by a shear, and shipped out as a coil. Accordingly, the inspection apparatus generates a defect map for each coil on the basis of information on a cut position, collates the defect map with a control standard such as the number of defects or a density, and determines whether shippable to a client for each coil. The image processing device 24 transmits a result of the determination to a shipping management department via an upper communication network.

In this embodiment, as described above, the steel sheet 30 is irradiated with the sheet-like light that has been linearly polarized at a predetermined polarization angle (for example, 45 degrees) by the polarizing filter 11, the reflected light is polarized by the polarizing filter 21, and linearly-polarized light at a polarization angle of about 0 degrees is imaged by the semi-regular reflection camera 22 at an acceptance angle shifted from the regular reflection angle of incident light by a predetermined angle. Accordingly, the reflection from the surface of the coating is suppressed, the abnormality in the coating itself is not observed, the substrate steel surface of the steel sheet 30 becomes observable, and highly accurate inspection becomes possible. Particularly, in this embodiment, a configuration of using linearly-polarized light at a polarization angle of about 45 degrees on a light source side, stabilizing a ratio between P-polarization and S-polarization to about 1:1 on the light source side, and causing light to enter at an angle avoiding Brewster's angle is employed. Accordingly, an effect of suppressing the reflection from the surface of the coating is stably obtained. According to the findings of the inventors of the present invention, this effect is approximately good when the polarization angle of the polarizing filter 11 is set to an angle in a range of 30 degrees to 60 degrees. The incidence angle of light from the sheet-like light source 10 is preferably set to be in a range of 40° to 85°.

In this embodiment, a steel sheet is irradiated with the sheet-like light from the sheet-like light source 10 at an incidence angle different from the Brewster's angle of the coating by 1 degree or greater, and inspection with stable reflection is enabled. A method of inspecting by setting Brewster's angle has the following problems, but these problems are all solved in this embodiment as described above.

(1) The Brewster's angle is a pinpoint and delicate angle at which reflection of P-polarized light becomes zero and setting thereof requires a precision of an incidence angle of less than 0.1 degrees. If the incidence angle is shifted from the Brewster's angle by 0.1 degrees, P-polarized light is reflected from the resin surface and the substrate steel surface of the steel sheet becomes inconspicuous. In industrial application for large-scale manufacturing lines of steel sheets, because maintenance of incidence angles is difficult, inspection results become unstable.

(2) Setting of a different Brewster's angle is necessary for each resin composition and thus the apparatus becomes complicated.

(3) Since patterns depending on thicknesses of resin are detected, sufficient inspection is difficult.

In this embodiment, by imaging the surface of a steel sheet at an angle shifted from the regular-reflection acceptance angle by a predetermined angle by the diffusion camera 23, highly accurate inspection becomes possible. By combining the imaging by the diffusion camera 23 and the imaging by the semi-regular reflection camera 22, even more highly accurate inspection becomes possible.

In this embodiment, stable surface inspection of a steel sheet coated with a resin is enabled as described above. Accordingly, a level of quality assurance for a client is improved and grasping product quality in real time becomes possible, and thus abnormalities in the processes are found earlier and the yield and productivity are improved.

Although the embodiment to which the present invention made by the inventor is applied to has been described, the present invention is not limited to the description and drawings, which constitute a part of the disclosure of the present invention by the embodiment. For example, other embodiments, examples, and operation techniques which may be made by those skilled in the art on the basis of the embodiment are all included in the scope of the present invention.

INDUSTRIAL APPLICABILITY

The present invention is applicable to surface inspection of a surface of a steel sheet coated with a transparent resin.

REFERENCE SIGNS LIST

10 SHEET-LIKE LIGHT SOURCE
11 POLARIZING FILTER
21 POLARIZING FILTER
22 SEMI-REGULAR REFLECTION CAMERA
23 DIFFUSION CAMERA
24 IMAGE PROCESSING DEVICE
30 STEEL SHEET

The invention claimed is:

1. A surface inspection method for inspecting a steel sheet coated with a resin by imaging the steel sheet coated with the resin and inspecting for a surface defect on a substrate steel surface of the steel sheet, the surface inspection method comprising:
   irradiating the steel sheet with sheet-like light that has been linearly polarized at a predetermined polarization angle; and
   imaging linearly-polarized light polarized by a polarizing filter having a polarization angle of 0 degrees at an acceptance angle shifted by 2 to 5 degrees with respect to a regular reflection angle of incident light, wherein the acceptance angle shifted by 2 to 5 degrees is smaller than the regular reflection angle, and
   wherein the steel sheet is irradiated with the sheet-like light at an incidence angle different from a Brewster's angle of the coating by 1 degree or greater.

2. The surface inspection method for the steel sheet coated with the resin according to claim 1, further comprising imaging a surface of the steel sheet at an angle shifted from the regular reflection angle by 10 degrees or greater.

3. A surface inspection apparatus for a steel sheet coated with a resin, which images the steel sheet coated with the resin and inspects for a surface defect on a substrate steel surface of the steel sheet, the apparatus comprising:
   a light source that irradiates the steel sheet with sheet-like light that has been linearly polarized at a predetermined polarization angle;
   a polarizing filter which has a polarization angle of 0 degrees and which linearly polarizes the light reflected from the steel sheet; and
   a first imaging device that images the light linearly-polarized by the polarizing filter at an acceptance angle shifted by 2 to 5 degrees with respect to a regular reflection angle of incident light, wherein the acceptance angle shifted by 2 to 5 degrees is smaller than the regular reflection angle, and
   wherein an incidence angle of the light source is set to an angle different from a Brewster's angle of the resin coating by 1 degree or greater.

4. The surface inspection apparatus according to claim 3, further comprising a second imaging device that images a surface of the steel sheet at an angle shifted from the regular reflection angle by 10 degrees or greater.

\* \* \* \* \*